United States Patent [19]
Loewy et al.

[11] Patent Number: 5,939,261
[45] Date of Patent: Aug. 17, 1999

[54] METHOD FOR CAPTURING A NUCLEIC ACID

[75] Inventors: Zvi Loewy, Fair Lawn; Rajan Kumar, Robbinsville, both of N.J.

[73] Assignee: Sarnoff Corporation, Princeton, N.J.

[21] Appl. No.: 08/881,282

[22] Filed: Jun. 24, 1997

[51] Int. Cl.$^6$ ............... C12Q 1/68; C07H 21/02; C07H 21/04; C12N 15/00
[52] U.S. Cl. ............ 435/6; 536/23.1; 536/24.3; 935/76; 935/77; 935/78
[58] Field of Search ............ 435/5, 6; 536/23.1, 536/24.3; 935/76, 77, 78

[56] References Cited

U.S. PATENT DOCUMENTS

| | | | |
|---|---|---|---|
| 4,868,105 | 9/1989 | Urdea et al. | 435/6 |
| 5,306,619 | 4/1994 | Edwards et al. | 435/6 |
| 5,635,352 | 6/1997 | Urdea et al. | 435/6 |
| 5,693,463 | 12/1997 | Edwards et al. | 435/6 |

OTHER PUBLICATIONS

Kinzler et al., Nucleic Acids Research 17(10): 3645–3653 (1989).
Wright et al., Molecular and Cellular Biology 11(8) : 4104–4110 (1991).
Wright et al., Trends in Biochemical Sciences 18 : 77–80 (1993).
Hobson et al., Analytical Biochemistry 193 : 220–224 (1991).
Sompayrac et al., PNAS 87 : 3274–3278 (1990).
Matthews et al., Analytical Biochemistry 169 : 1–25 (1988).
Ledbetter et al., Genomics 6 : 475–481 (1990).
The Dynal Catalog and Technical Handbook, 2nd Edition, pp. 106–115 and Appendices A and B (1995).
Giraldo et al., "The yeast telomere–binding RAP1 binds to and promotes the formation of DNA quadruplexes in telomeric DNA", *The EMBO Journal*, 13: 2411–2420, 1994.
Wagner et al., "Mutation detection using immobilized mismatch binding protein (MutS)", *Nucleic Acids Research*, 23: 3944–3948, 1995.
Kadonag et al., "Promoter–specific activation of RNA polymerase II transcription by Sp1", *Trends in Biochemical Sciences*, 11: 20–23, 1986.
Thiesen et al., "Target Detection Assay (TDA): a versatile procedure to determine DNA binding sites as demonstrated on SP1 protein", *Nucleic Acids Research*, 18: 3203–3209, 1990.
Briggs et al., "Purification and Biochemical Characterization Of the Promoter–Specific Transcription Factor, Sp1", *Science*, 234: 47–52, 1986.
Britten et al., Repeated Sequences in DNA, *Science*, 161: 529–540, 1968.
Jelinek, et al., "Repetitive Sequences In Eukaryotic DNA and Their Expression", *Ann. Rev. Biochem.*, 51: 813–844, 1982.
Britten et al., "Sources and evolution of human *Alu* repeated sequences", *Proc. Natl. Acad. Sci. USA*, 85: 4770–4774, 1988.
Singer, "SINEs and LINEs: Highly Repeated Short and Long Interspersed Sequences in Mammalian Genomes", *Cell*, 28: 433–434, 1982.
Korenberg et al., "Human Genome Organization: Alu, Lines, and the Molecular Structure of Metaphase Chromosome Bands", *Cell*, 53: 391–400, 1988.

*Primary Examiner*—W. Gary Jones
*Assistant Examiner*—Ethan Whisenant
*Attorney, Agent, or Firm*—William J. Burke

[57] ABSTRACT

The present invention relates to a method for capturing a class of nucleic acids comprising (a) providing a population of nucleic acids, wherein the population comprises the class; (b) binding a probe moiety to nucleic acids of the class, thereby forming one or more complexes, wherein the probe moiety is attached to a substrate; and (c) capturing the complex. The method can be implemented in certain embodiments in a structure comprised of one or more reservoirs, preferably wherein the reservoirs include one or more second chambers that are in communication with a first chamber. Preferably, the present invention is used to capture the class of nucleic acids that comprise regulatory elements included in a population of nucleic acids isolated from a cell, tissue, or organism. An alternative preferred embodiment of the present invention involves the capture of the class of nucleic acids that comprises certain repetitive elements included in a population of nucleic acids derived from an organism.

19 Claims, 1 Drawing Sheet

METHOD FOR CAPTURING A NUCLEIC ACID

This patent application is related to the following copending U.S. patent applications: Ser. No. 08/556,036, filed Nov. 9, 1995, entitled A PARTITIONED MICROELECTRONIC DEVICE ARRAY (Zanzucchi et al.); Ser. No. 08/556,423, filed Nov. 9, 1996, entitled ELECTROKINETIC PUMPING (Zanzucchi et al.); Ser. No. 08/645,966, filed May 10, 1996, entitled ELECTROKINETIC PUMPING (Zanzucchi et al.); Ser. No. 08/483,331, filed Jun. 7, 1995, entitled METHOD AND SYSTEM FOR INHIBITING CROSS-CONTAMINATION IN FLUIDS OF COMBINATORIAL CHEMISTRY DEVICE (Demers); Ser. No. 60/009,517, filed Nov. 3, 1995, which is the priority document for a regular application filed Nov. 1, 1996, and both of which are entitled ASSAY SYSTEM (Roach et al.); Ser. No. 08/745,766, filed Nov. 8, 1996, entitled FIELD-ASSISTED SEALING (Fan et al.); Ser. No. 08/786,956, filed Jan. 22, 1997, entitled PARALLEL REACTION CASSETTE AND ASSOCIATED DEVICES (Southgate et al.); Ser. No. 08/742,971, filed Nov. 1, 1996, entitled MAGNET (McBride); Ser. No. 08/554,887, filed Nov. 9, 1995, entitled METHOD OF PRODUCING MICRO-ELECTRONIC CONDUITS (Thaler et al.); Ser. No. 08/664,780, filed Jun. 14, 1996, entitled AUTOMATED NUCLEIC ACID SOLUTION (Southgate et al.); Ser. No. 08/730,636, filed Oct. 11, 1996, entitled LIQUID DISTRIBUTION SYSTEM (Demers et al.); and Ser. No. 08/838,102, filed Apr. 15, 1997, Method For Translocating Microparticles In A Microfabricated Device (Fan et al.).

This invention was made with U.S. Government support under Contract Nos. N66001-96-C-8630 and 70NANBH1037. The U.S. Government has certain rights in this invention.

The present invention relates to the field of nucleic acid identification. In particular, the present invention relates to a method for the capture of one or more nucleic acid species in a sample, after which the identity or identities of the captured nucleic acids can be determined. In a preferred embodiment, the present invention relates to the capture of nucleic acid species, wherein the method is conducted in a microfluidics environment.

As a first step in the identification of a nucleic acid, one must capture the nucleic acid population that includes the species that is being sought. A difficulty of current methods includes what appears to be opposite problems: Current methods for capturing a population of nucleic acids are commonly either completely nonspecific and are thus overinclusive, or exquisitely specific and are therefore underinclusive for the purpose of capturing an enriched population from which a nucleic acid of interest can be identified. The present invention provides a solution to these and other difficulties, as described hereinbelow.

SUMMARY OF THE INVENTION

The present invention provides a method for the capture of a class of nucleic acids found in a biological sample. In one embodiment, the present method uses as little as microliter or nanoliter volumes of sample and reagents. Moreover, the low volume method is adaptable for use in a closed environment of a cassette or microfabricated device, thus allowing a greater degree of safety in the diagnosis of potentially infectious agents.

In particular, the present invention relates to a method for capturing a class of nucleic acids, comprising (a) providing a population of nucleic acids comprised of nucleic acids of the class; (b) binding a probe moiety to nucleic acids of the class, thereby forming one or more complexes; and (c) capturing the complex; wherein the nucleic acids of the population are attached to a substrate and the probe moiety is a DNA binding protein or a repetitive nucleic acid element. Preferably, this method is effected in a structure comprising a reservoir. Further, this method is preferably effected wherein the substrate is a paramagnetic or superparamagnetic microparticle. Yet further, this method is preferably effected wherein the probe moiety binds preferentially to a specific sequence.

Yet another embodiment relates to a method for predicting transcription efficiency of a regulatory element identified as above, comprising hybridizing a first nucleic acid having the regulatory element to a second nucleic acid having a regulatory element consensus sequence in the presence of a mismatch binding protein, such as MutS protein.

DETAILED DESCRIPTION

Figure 1:
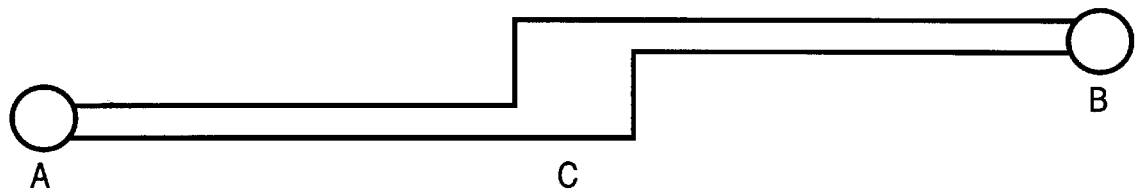
FIG. 1 depicts a generic device for nucleic acid detection.

Detection of particular nucleic acids has importance for the diagnosis and treatment of disease, control and testing of quality and contamination issues regarding food and medicinal products, as well as the conduct of broad areas of biotechnical research. Accordingly, new methods for capturing nucleic acids, such as those disclosed herein, are useful for these various product areas and pursuits. In particular, the present invention is directed to the capture of a class of nucleic acids that can be present in a broader population of nucleic acids. Such populations preferably comprise genomic deoxyribonucleic acid (DNA) preparations derived from any cell, tissue or organism using conventional methods of isolating or preparing same. Alternative such populations of nucleic acids include complementary DNA (cDNA) populations derived by action of reverse transcription on a population of ribonucleic acid (RNA), preferably messenger RNA (mRNA), ribosomal RNA (rRNA), or transfer RNA (tRNA). The population of nucleic acids subjected to the instant method can also be RNA, such as mRNA, rRNA, and tRNA. Classes of nucleic acids that can be captured by the present method include, for example, nucleic acids that include regulatory elements, particularly regulatory elements that have control over the conduct or efficiency of transcription, heterochromatin, telomers, centromeres, and the like. See, for example, Giraldo et al. and *Embo* $5^1$, 13, 2411–24201 (1994).

Such classes of nucleic acids, as can be understood by reviewing the list, are defined with respect to the binding characteristics associated with proteins whose biological function is to bind nucleic acid. The function of these DNA binding proteins is to regulate transcription or effect other genetic functions as indicated above.

Another category of classes of nucleic acids that can be captured using the present invention is identified using probe moieties comprised of a nucleic acid that hybridize to complementary single stranded nucleic acids. Preferably, such nucleic acid probe moieties are comprised of repetitive elements, which are further discussed hereinbelow.

In one embodiment, the present invention provides methods by which samples of nucleic acid can be determined to be derived from one species versus another by, for example, using the aforementioned repetitive nucleic acid elements as probe moieties, where the repetitive nucleic acid elements so used are known to identify human-derived DNA versus DNA derived from another source, for example. The same method can be used to capture the complete or the substantially complete complexity of the genome of an organism being subjected to genetic analysis. Another embodiment of the present invention, as noted above, provides a method to identify regulatory elements from mixtures of nucleic acids, preferably by using a DNA binding protein as a probe moiety. Further, in yet another embodiment of the present invention, the strength of transcription efficiency can be determined for a gene whose regulatory element has been identified using the aforementioned method, for example, and then hybridizing the nucleic acid that includes the identified regulatory element to a regulatory element consensus sequence, as further described below, in the presence of a mismatch binding protein, such as the MutS protein described in Wagner et al., Nucleic Acids Research, 23, 3944–3948 (1995).

In particular, the present invention relates to a method for capturing a class of nucleic acids, comprising (a) providing a population of nucleic acids, comprised of nucleic acids of the class; (b) binding a probe moiety to nucleic acids of the class, thereby forming one or more complexes, wherein the probe moiety is attached to a substrate; and (c) capturing the complex; wherein the probe moiety is selected from the group consisting of a DNA binding protein or a repetitive nucleic acid element.

The population of nucleic acids from which the class of nucleic acids is captured in the context of the present invention is preferably comprised of ribonucleic acid ("RNA") or deoxyribonucleic acid ("DNA"), either of which can be isolated from a natural source, such as a cell or a virus, or can be synthetic using chemical or enzymatic means known in the art. More preferably, the RNA can be any variety of RNA, such as, but not limited to, messenger RNA, transfer RNA, or ribosomal RNA. Alternatively, the DNA can be genomic DNA isolated directly from a natural source, such as a cell, tissue, or organism, or synthesized using known methods of nucleic acid chemistry. Such RNA or DNA include those sequences derived from nuclear, mitochondrial, or chloroplast genomes, DNA that is complementary to an RNA sequence resulting from a reverse transcription, or any RNA found in the cell, tissue, or organism. Additionally, the population of nucleic acids can comprise a molecule having both proteinaceous and nucleic acid components.

Whatever the source of the population of nucleic acids, it can be provided as uncut nucleic acid or subjected to random shearing or nuclease attack. If subjected to nuclease attack, the nuclease products are the result of any suitable digestive enzyme of a nucleic acid, such as, but not limited to, restriction endonucleases, other DNA endonucleases, DNA exonucleases, and RNA endo- and exonucleases. The first nucleic acid can also be provided as amplicons, i.e., the result of a polymerase chain reaction ("PCR") and the like, as known in the art.

Preferably, in an embodiment of the invention directed toward identifying or capturing regulatory elements of genes, the probe moiety is a DNA binding protein. Preferred DNA binding proteins include SP1, C-FOS, WT-1, or CRO. Preferred DNA binding proteins are known to specifically bind to regulatory elements, and such proteins include both repressors and enhancers of transcriptional activity. For example, SP1 protein is prevalent in eukaryotic cells, and binds to polynucleotide motifs that include the GC box, the consensus sequence for which is GGGCGG. Kadonaga et al., *Trends Biochem. Sci.,* 11, 20–23 (1986); Thiesen et al., *Nucleic Acids Res.,* 18, 3203–3209 (1990); and Briggs et al., *Science,* 234, 47–52 (1986). The GC box is believed to affect the efficiency of transcription in eukaryotic genes, although it is not universally present in such genes. Other regulatory elements that can be identified include inducible elements, such as, but not limited to, steroid hormone control sites, such as occurs in the control of certain sex-limited gene activities. Typically, a steroid hormone, such as estrogen, testosterone, or β-ecdysone, has a specific protein receptor molecule that it binds to, and in the receptor-bound state, migrates to the nucleus where the receptor-hormone complex interacts with the genome and affects gene activity. Accordingly, other DNA binding proteins preferably used in the context of the present invention include steroid hormone receptors, although such proteins are preferably applied in the presence of a suitable concentration of the appropriate hormone. See Kadonaga et al., supra; Thiesen, supra; and Briggs et al., supra.

Another embodiment of the present invention employs repetitive nucleic acid elements as the preferred probe moiety, wherein the repetitive nucleic acid element is the unit nucleic acid sequence that is repeated in a given genome. Such elements are included in the nuclear genome of all multicellular eukaryotes, the repeat pattern of which can be tandem at a particular site or sites, which site or sites can be found on a particular chromosome or chromosomes, or on all chromosomes, such as at heterochromatin sites or telomeres. Repetitive DNA elements occur repeatedly in the chromosomal DNA and are characterized by (1) the number of base pairs (bp) per repeated element, ranging from about 7 bp to about 500 bp; (2) the specific order of bp per repeated element, and (3) the number of copies of a repeated element per genome. Repetitive DNA elements preferably used in the context of the present invention are interspersed throughout the genome. Respective DNA elements comprise 20–50% of most animal genomes and more than 50% of many plant genomes. They include many structural genes constituting multigene families and may be present either in tandem arrays (as in satellite DNA) or interspersed within other sequences. As used in the context of the present invention, repetitive elements do not include transposable genetic elements or those elements that are not distributed in at least 50% of the chromosome present in a multicellular organism of interest; preferably, at least 75% of the chromosomes include such repetitive elements; more preferably, at least 90% of the chromosomes include such repetitive elements; and most preferably, all of the chromosomes include such repetitive elements.

Repetitive DNA elements generally fall into four commonly occurring classes as noted by Britten and Kohne, *Science,* 161, 529 (1968): (1) The repeated structural genes; (2) the interspersed middle repetitive sequences; (3) the tandemly repeated highly repetitive sequences; (4) the inverted repeat of foldback sequences. Preferably, repetitive elements used in the context of the present invention are of the second or third class, more preferably of the second class.

The distribution of repetitive DNA families over the eukaryotic genome is highly diverse. Some families are confined to heterochromatic regions, others occur in complex interspersion patterns with each other and with single copy DNA. The present invention preferably includes use of nucleic acids that define or can hybridize to family members of the latter sort.

As noted above, preferred repetitive elements include those classified as middle or moderately repetitive DNA.

Moderately repetitive DNA exists in two different patterns: (1) Short-period interspersion (mammals, most vertebrates, and sea urchins) in which about 300 bp-long sequences are interspersed with unique sequence DNA that is from about 1000 to about 3000 bp long; (2) long-period interspersion in which the repetitive sequences are longer than 1.5 kb and show less divergence than the short DNA sequences. The two interspersion patterns are called SINE's and LINE's, respectively; the former include the primate and rodent Alu-like sequences, the latter proviral type and L1 sequences.

Members of a diverse array of repeated sequence families often show a high degree of homogeneity, yet differ substantially between related species. Thus, as used in the context of the present invention, particular repetitive elements can be used as a probe to select for the DNA of a particular species. For example, the AZV family of repeats of which a consensus sequence has been determined. See, for example, Jelinek, *Ann. Rev. Biochem.,* 51, 813–844 (1982); and Britten et al., *Proc. Narl. Acad. Sci. USA,* 85, 4770–4774 (1988).

Highly repetitive DNA sequences can be separated into two general classes based on their complexity: (1) Simple sequence repetitive DNA composed of short (about 7 to about 20 bp) segments extensively repeated, usually with some divergence, in a tandem fashion that often gives rise to longer periodicities; (2) a longer more complex repetitive DNA.

One preferred class of repetitive elements is known as variable number tandem repeat ("VNTR") sequences. VNTR sequences are known to be polymorphic, and have been used extensively in the field of forensics with respect to questions of identity. Another preferred class of repetitive elements is known as the ALU family of repeats. ALU sequences are abundant, ranging between 300,000 and 500,000 repeats per human genome, and has a published consensus sequence. See, for example, Britten et al., supra.

Because of the extensive distribution of the ALU repeats in the human genome, one can use a core consensus sequence as a probe to selectively capture human genomic DNA, and due to the ubiquity of such sequences, the copy number of ALU sequences per genome provides a natural enrichment process.

Preferably, the probe moieties are attached to a surface, such as a membrane, a well of a microwell plate, or a microparticle. The binding of a probe moiety can be accomplished using any of various methods known in the art, including, but not limited to, combining a biotinylated probe moiety, such as an oligonucleotide having the ALU consensus sequence, with a microparticle having attached thereto streptavidin. Other methods of specifically attaching a nucleic acid or protein probe onto a surface as set forth herein are well known in the art.

As noted above, collecting or capturing the nucleic acid sequences found adjacent to a class of repetitive elements provides a natural enrichment of a definable fraction of the human genome, which itself provides a new approach to the assessment of viral integration patterns, location of oncogenes, and other genetic analyses.

In a preferred embodiment of the present method, the present invention provides a method for capturing a class of nucleic acids within the confines of a structure comprised of one or more reservoirs, such as a first chamber that is preferably included in a standardized miniaturized (referred to as a "cassette") or microfabricated (referred to as a "chip") structure which is comprised of chambers and channels, as described in Ser. Nos. 08/742,317 and 08/664,780 with respect to the cassette, and Ser. Nos. 08/483,331 and 08/554,887 with respect to the chip. A representation of such a structure is provided by FIG. 1, wherein A and B represent second chambers, C represents a first chamber, and the narrow lanes that respectively connect A and B to C are fluid exchange channels. Each type of chamber and the channels are further defined below.

This capture method is particularly useful because it facilitates the identification of two or more different classes of nucleic acids or segments thereof simultaneously or sequentially within the same biological sample, within which the detection of the nucleic acids of interest is sought. Another feature of the present invention is its ability to identify nucleic acids that include a regulatory element.

The present invention can be practiced in the context of either a cassette or a chip, the essential difference between the two being the quantity of sample and reagents used, and the sizes of the channels and reservoirs included therein. In certain embodiments, a reservoir functions as a reaction site, referred to herein as a "first chamber". A reservoir can also function as a storage site for reagents or a waste receptacle, each of which reservoirs are referred to herein as a "second chamber". In certain embodiments, a particular chamber can function as a site for a reaction, thus be a first chamber, yet in another stage of the method as thus embodied, the same chamber can function as a waste receptacle, thus be a second chamber.

The reservoirs used in a cassette or chip are one or more first chambers, in which reactions relating to the identification method can take place, although the same reactions can also take place in second chambers or channels, depending on the design used in a particular embodiment. The cassette or chip used in the context of the present invention also includes at least one second chamber, which contain reagents used in the identification method, or are used as a receptacle for waste that results from the identification method. Again, the same second chamber that initially was a storage facility for reagents at a prior stage of the method can serve as a waste receptacle, or as a reaction chamber, or both at varying times. Simply put, the cassette and chip design provides much latitude for design variations for placement of first or second chambers and interconnecting fluid exchange channels. Valves, both of a reversible and irreversible sort, can be used in this context, including Bursapak™-type chambers that provide their own irreversible "valve." See Ser. Nos. 08/742,317 and 08/664,780.

More particularly with respect to the cassette used in the context of the present invention, the cassette itself can be made of any suitable material having characteristics of sufficient moldability for forming the cassette, sufficient strength and resistance to chemical attack, and the like; for example, the cassette is preferably formed of a molded plastic, such as high density polyethylene, but other materials that are suitably resistant to the chemistries used in nucleic acid identification, such as glass and silicon-based materials, can be used. Where the cassette is formed of plastic, it is preferably formed by a molding process that is used to form cavities and channels that will be sealed with upper and lower plastic films to form second chambers and fluid exchange channels. Such cavities and channels are formed in suitable materials, such as glass and silicon materials, by chemical etching or laser ablation. Upper and lower films typically have a thickness of from about 0.3 mils to about 5 mils, preferably from about 1 mil to about 3 mils. For chambers having a diameter of about 1 cm or more, the film thickness is more preferably about 2 mils. The first chamber, in which the reactions relating to the nucleic acid preparation take place, typically has a thickness, between the upper and lower films, of from about 0.1 mm to about 3 mm, preferably of from about 0.5 to about 1.0 mm, and an area, defined by the inner surface of the upper or lower films, of preferably from about 0.05 cm$^2$ to about 2 cm$^2$, more preferably from about 0.1 cm$^2$ to about 1 cm$^2$, yet more preferably about 0.5 cm$^2$. The dimensions of the first chamber are preferably sized small enough to permit rapid throughput of fluids so that the chemical conditions of the substrates having probe moieties or first nucleic acid, depending on the embodiment being practiced, attached thereto can be exchanged predictably and rapidly (on the order of about one to about 10 seconds). Preferably, the total volume of each first chamber in a cassette is between about 5 μl and about 250 μl, more preferably, between about 10 μl and about 100 μl. Preferably, each first chamber has a thickness (i.e., distance between upper film and lower film) of about 1 mm or less.

Fluid exchange channels in a cassette typically describe a cylinder and have a diameter between about 200 μm and about 500 μm; alternatively, the channels can be constructed in other shapes having a width or depth respectively of from about 200 μm to about 500 μm. Second chambers typically have a volume capacity between about 5 μl and about 500 μl, preferably from about 10 μl to about 200 μl, more preferably from about 30 μl to about 160 μl. The second chambers can contain reagents required in the identification of the nucleic acid, such as hybridization reagent, wash fluid, microparticles, Tris-EDTA (TE) buffer, and the like; such reagents can be contained in the second chambers in dry or liquid form, and if in dry form, can be constituted with water or other liquid reagent contained in other second chambers, or from water or other liquid reagent delivered from an external source. Second chambers used for metering a given volume preferably have a volume between about 5 μl and about 50 μl.

The upper and lower films preferably are resistant to temperatures at least as high as about 120° C. and are between about 0.5 and about 4 mils in thickness, more preferably, between about 1 and about 3 mils. The thinness of the membranes facilitates rapid heat exchange between the first chamber, or wherever the reactions to be effected within the cassette are to be located, and an adjacent heating or cooling device, which can be used to establish a constant temperature for the sample of nucleic acid being tested, if desired.

The cassette comprising the aforementioned first chambers, second chambers, including supply, waste, and metering chambers, fluid exchange channels, and the valves and pumps further discussed previously (see Ser. No. 08/664,780), can have any suitable design. Indeed, any cassette design that includes at least one second chamber, at least one first chamber, and means of communication therebetween (i.e., the fluid exchange channels) suitable for the identification of a first nucleic acid is preferred. More preferred, the cassette comprises up to six wells for entry of a sample container and its contents, which are connected to one or more first chambers into which the first nucleic acid is distributed, and where the first nucleic acid is contacted by probe moieties stored in second chambers, which probe moieties are second nucleic acids that are specific for different target nucleic acids or segments thereof that may be contained within the mixture of nucleic acids combinedly referred to as the first nucleic acid. Alternative probe moieties set forth herein are DNA binding proteins, as discussed above.

Alternatively, the microfabricated device, i.e., the chip, used in the context of the present invention preferably includes channels filled with fluid, wherein the channels are preferably less than about 300 μm wide and less than about 300 μm deep. The microfabricated device can be constructed of any suitable material or combination of materials, including but not limited to a glass, plastic, and the like, wherein a suitable material is substantially rigid at room temperature (about 25° C.) up to at least about 40° C., and remains a solid at a temperature of up to at least about 120° C. In addition to the channels included in the microfabricated device, a preferable device comprises reservoirs, including a first chamber and one or more second chambers that are interconnected by the channels. The first chamber is alternatively referred to as the reaction chamber, however, one of the advantages of the present method is the ability to use any chamber or any channel or portions thereof as the site of the reactions needed for the diagnostic procedure, as further discussed below. The second chambers are alternatively referred to as supply or waste chambers. The aforementioned material from which the chip is constructed can vary at or about the chambers, such as, for example, including at least one deformable wall at a chamber, preferably a second chamber. Preferably, the chip has at least two second chambers that have a deformable wall.

The first chamber of a chip preferably has dimensions of from about 25 μm to about 10 mm wide, from about 25 μm to about 10 mm long, and from about 5 μm to about 500 μm deep. More preferably, the first chamber has dimensions of from about 50 μm to about 5 mm wide, from about 50 μm to about 5 mm long, and from about 10 μm to about 300 μm deep. Yet more preferably, the first chamber has dimensions of from about 100 μm to about 1 mm wide, from about 100 μm to about 1 mm long, and from about 20 μm to about 100 μm deep. The volume capacity of the first chamber of a chip is preferably from about 0.05 μl to about 50 μl; more preferably, from about 0.1 μl to about 10 μl; yet more preferably from about 0.1 μl to about 1 μl.

The second chambers have any suitable dimensions such that sufficient reagents and waste chambers are thereby provided in the chip for the nucleic acid identification protocol for which the chip is designed. In most applications, volume requirements of the second chambers preferably will not exceed about 500 μl; more particularly, second chambers used for waste disposal preferably have a volume capacity of from about 200 μl to about 500 μl, whereas second chambers used for reagent storage preferably have a volume capacity of from about 50 μl to about 250 μl.

The channels included in the chip preferably have dimensions of from about 5 μm to about 500 μm wide, from about 5 μm to about 500 μm deep, and from about 500 μm to about 250 mm long. More preferably, the channels included in the chip preferably have dimensions of from about 15 μm to about 300 μm wide, from about 10 μm to about 300 μm deep, and from about 1 mm to about 100 mm long. Most preferably, the channels have dimensions of from about 30 μm to about 150 μm wide, from about 20 μm to about 100 μm deep, and from about 5 mm to about 50 mm long. The channels can be situated colinear or not colinear with respect to the first chamber. For example, for one embodiment that has a colinear arrangement of channels and chambers, all of the channels and chambers would be aligned in the same plane as one that is parallel with the wall of the chip. In contrast, an alternative embodiment that has a non-colinear arrangement can have a chamber situated adjacent to one wall of the chip and all or some of the channels situated adjacent to the other wall of the chip, i.e., the channels or some of the channels are situated in different planes than is at least one of the chambers. In such an embodiment, the channel would connect to a chamber by a bend away from a parallel plane with the adjacent wall, bending toward the chamber. Alternatively, channels connected to a chamber can interface the chamber such that one channel can be connected to opposite corners of, for example, a square or cube shaped chamber.

As can be appreciated from the above discussion concerning the preferred components and dimensions of cassettes and chips, which collectively are referred to herein as "structures," the present method is suitably conducted in either context. In particular, the present invention relates to a method for detecting a first nucleic acid or a segment thereof in a suitable structure comprised of a first chamber, which is preferably in fluid communication with one or more second chambers, i.e., the aforementioned cassette or chip, comprising (a) providing the first nucleic acid, (b) binding a probe moiety to the first nucleic acid, thereby forming a complex, wherein the probe moiety is attached to a substrate; and (c) detecting the complex. This method preferably is practiced in the context of a structure that further comprises one or more second chambers that are in communication with the first chamber. Attachment of the probe moiety to the substrate can be done prior to inserting the probe moiety into the structure; alternatively, the probe moiety is attached to the substrate in the device.

As set forth above, the present invention is preferably conducted in the context of a structure comprised of a first chamber or more preferably, further comprised of one or more second chambers. The structure is referred to herein as a removable chemistry cassette or a microfabricated device, one of the distinguishing features of which are the range of sizes of the included chambers and fluid exchange channels. For example, whereas the generic structure preferably includes a first chamber having a volume of from about 0.05 $\mu$l to about 250 $\mu$l, the first chamber of a chip preferably has a volume of from about 0.1 $\mu$l to about 10 $\mu$l and that of a removable cassette has a volume of from about 10 $\mu$l to about 100 $\mu$l.

The surface or substrate used in the context of the present invention is preferably a microparticle. A microparticle can have any shape, which is preferably spherical and when spherical, it is referred to as a "bead." Preferably, the microparticle has no dimension in excess of about 500 $\mu$m; and more preferably, of less than about 100 $\mu$m. In certain preferred embodiments, the microparticles have a maximum dimension of from about 0.5 $\mu$m to about 25 $\mu$m, and more preferably from about 1 $\mu$m to about 5 $\mu$m, and even more preferably, about 2 $\mu$m to about 4 $\mu$m. Accordingly, beads used in the context of the present invention have diameters in accordance with the aforementioned maximum dimensions. Microparticles are comprised of any suitable material, the choice of material being guided by its characteristics, which preferably include minimal non-specific adsorptive characteristics with respect particularly to proteins or nucleic acids, such as that of polystyrene. In other embodiments, the microparticles are comprised of, for example, glass, cellulose or a cellulose derivative, plastic, such as nylon or polytetrafluoroethylene ("TEFLON"), metal, ceramic and the like, and combinations thereof.

A preferred microparticle used in the context of the present invention is magnetic. More preferably, the microparticle is paramagnetic. A paramagnetic microparticle can be comprised of, for example, iron dispersed in a polystyrene matrix, and can be obtained, for example, from Dynal (Oslo, Norway). Yet more preferably, the microparticle is superparamagnetic, where the distinction between paramagnetic and superparamagnetic microparticles is that the former retain some magnetic attraction after a magnetic field has been removed and thus tend to clump or remain clumped, whereas the latter have no remanence in the absence of the magnetic field and thus are readily dispersed after a magnetic field is removed.

The preferred microparticle has a moiety attached thereto. A suitable moiety includes a means for binding the microparticle to defined molecules, such as a probe that preferentially binds to the first nucleic acid, more preferably to a particular segment included in the first nucleic acid, which moiety is referred to herein as a probe moiety. A probe is a molecule that preferentially binds to a particular sequence of a nucleic acid, such as an oligonucleotide that under appropriate conditions hybridizes to a nucleic acid that includes a segment that is complimentary to at least a portion of the oligonucleotide. Other exemplary probes are discussed below. An alternative moiety includes a means for signalling the presence of the microparticle, which alternative moiety is referred to herein as an indicator moiety. The moiety can also be a chemical species that preferentially or, yet more preferably, exclusively binds to a second chemical species, for the purpose of attaching, for example, an indicator or probe moiety to the substrate. A moiety that so binds to the second chemical species is herein referred to as a binding moiety, which can be, but is not limited to, avidin, biotin, streptavidin, fluorenylmethoxycarbonyl (FMOC), an antibody, Protein A, or a lectin.

Overall, any aforementioned embodiment of the moiety comprises an organic or inorganic compound. Preferably, such a compound comprises an amino acid, a polypeptide, a nucleotide, a nucleoside, a nucleic acid, a carbohydrate, or an organic compound, or a combination thereof, such that it is a probe, an indicator, or a chemical species that preferentially or exclusively binds to a second chemical species.

Preferably, the probe or indicator attaches to the substrate by means of a covalent linkage. Such a linkage can be direct between the probe or indicator to a component of the substrate. Alternatively, the linkage can be indirect by means of a binding moiety as set forth above. A preferred embodiment of such an indirect means comprises the covalent attachment to the substrate of a binding moiety that preferentially or, more preferably, exclusively binds to a second chemical species that is covalently attached to the probe or indicator moiety. For example, avidin can be attached to the substrate and biotin can be attached to the probe or indicator; the combining of the so-constructed substrate and probe or indicator will result in linked substrate and probe or indicator, possibly both, using procedures well known in the art.

The preferred means for capture of a particular class of nucleic acids is to combine the population of nucleic acids and a probe moiety under conditions whereby the nucleic acid and probe will attach (hybridize) to one another. Such attachment is mediated by hybridization if the probe is itself a nucleic acid, or comprises a nucleic acid, that includes at least a segment that is complementary to a segment of a subset of the aforementioned population of nucleic acids. Alternatively, if the probe is a protein, the probe otherwise recognizes or binds to a segment included within the population of nucleic acids. Preferably, the probe recognizes a specific sequence that is unique in a genome of interest, or is multiply represented in the genome of interest. In other embodiments, the probe recognizes a consensus sequence of a regulatory element, for example, wherein certain residues of the consensus sequence varies within certain parameters, as is known in the art. Preferred protein probes include, but are not limited to, Sp1, C-FOS, WT-1, or CRO, which are proteins known to regulate gene expression in eukaryotic or prokaryotic systems.

As noted above, the substrate can include an indicator moiety; the nucleic acids of the aforementioned population can also include an indicator moiety. In the context of the present invention, the indicator moiety can be attached to the nucleic acids of the population, or to the substrate or probe, or to the nucleic acids of the population and the substrate or probe, or to all three. Thus, the population of nucleic acids, probe or substrate includes an indicator moiety, provided that distinguishable indicator moieties are used when at least two of the population of nucleic acids, probe, and substrate include an indicator moiety. Preferably, the indicator moiety is fluorescent, radioactive, or a substance that causes a color or light change, embodiments of which are well known in the art. Distinguishable indicator moieties used in the context of the present invention can be any combination of the aforementioned indicator moieties, including radioactive indicators, e.g., radioactive isotopes of phosphorus, carbon, hydrogen, sulfur, and the like, fluorescent indicators, e.g., rhodamine, fluorescine, and the like, and enzymes that cause a color or light change under appropriate conditions and in the presence of appropriate substrates, e.g., alkaline phosphatase, luciferase, and the like. By "distinguishable" it is intended that different indicator moieties can be used to identify those nucleic acids captured by one probe moiety versus another, as in having a radioactive hydrogen included in an indicator moiety that is attached to a first probe moiety complexed to one set of nucleic acids; which can be distinguished from a second probe moiety complexed to a different set of nucleic acids if the second probe moiety includes, for example, a radioactive carbon or a fluorescent tag, such as rhodamine or fluorescine.

Detecting the presence of a captured class of nucleic acids, wherein the class of nucleic acid has attached to the probe thereby forming a complex, comprises exposing a suitable detector to the complex, wherein the detector is a detector of radiation, fluorescence, or light, which are known in the art.

As noted above, one of the important features of the present invention is its applicability to the capturing of differing classes of nucleic acids of a population of nucleic acids by use of two or more different probes. For this aspect of the invention, the substrate with attached probe moiety is preferably distributed to two or more different first chambers, wherein the probe within a particular first chamber is the same, but differs from the probe found in other first chambers. This distributing of the probe can be accomplished in various ways in the context of the aforementioned structure, including inserting into the structure substrate and probes separately or inserting the substrate and probes in a pre-attached form in separate aliquots.

One approach to the distribution is to form the structure including a precise quantity of substrate having a binding moiety in each first chamber, wherein the number of such first chambers so used equals the number of different probes used to test the nucleic acid and the quantity of the binding moiety per substrate is substantially the same comparing one substrate to another. The inclusion of equal quantities of the substrate in each first chamber can be measured if an indicator moiety is also attached to the substrate, wherein the quantity of indicator moiety per substrate is substantially constant, and each first chamber is accordingly scored for equal presence of the indicator moiety by measurement of the indicator. The probes can be prepared having attached thereto a second binding moiety that will preferentially, preferably exclusively, attach to the binding moiety attached to the substrate. Then, by adding the so prepared probe into the structure, and causing the probe to flow into a particular first chamber under conditions that favors attachment between the aforementioned binding moieties, and repeating these steps for other probes that are placed into other first chambers, each first chamber will be charged with substantially equal quantities of the respective probes. One alternative includes the use of different pairs of binding moieties that exclusively bind inter se, wherein different probes that separately have attached thereto the appropriate binding moieties will attach to the appropriate binding moiety bound substrate such that each first chamber will include homogenous probe species by flowing all probes as a group from one first chamber to the next. Other approaches can provide the same result, including the use of metering chambers to quantify amounts of fluids or suspensions, use of suitable magnets to move or hold in place quantifiable amounts of magnetic substrates with attached probes, and the like, which can be applied by those skilled in the art.

As set forth above, the various first chambers having aliquots of the probe or population of nucleic acids, depending on the embodiment, included therein in substantially equal numbers are then infused with the same population of nucleic acids or different probes, respectively, thereby placing the different probes in the respective first chambers in contact with the same population of nucleic acid sequences. As noted, the different probes recognize different sequences contained in the population of nucleic acids, including, preferably, those that comprise regulatory elements, are complementary to repetitive elements, and the like.

An alternative embodiment of the present invention comprises distributing the population of nucleic acids attached to a substrate to various reservoirs, followed by flowing different probes as above into each of the reservoirs, wherein, for example, the different probes test for the presence of different nucleic acid sequences. Essentially, the same techniques discussed above for the distribution of probes attached to the substrate operate with respect to this embodiment's requirement to distribute, instead, the population of nucleic acids attached to substrate into various reservoirs.

The present invention is further related to a method for predicting transcription efficiency of a regulatory element identified according to the method recited hereinabove, comprising hybridizing a first nucleic acid having the regulatory element to a regulatory element consensus sequence in the presence of a mismatch binding protein, preferably the MutS protein disclosed by Wagner et al., supra. A mismatch binding protein is a protein that preferentially binds to a portion of a double-stranded nucleic acid, wherein the portion includes mismatched, i.e., non-complementary, basepairs.

The present invention is intended to be practiced in the context of standard nucleic acid chemical methods, as noted hereinabove. Artisans of ordinary skill in this art regularly follow protocols recited in the contemporary technical literature, as well as refer to protocols set forth in generally available publications of molecular biology and biotechnology laboratory protocols, such as, but not limited to, Ausubel et al., *Short Protocols In Molecular Biology* (1992) and Sambrook et al., *Molecular Cloning: A Laboratory Manual* (2d ed., 1989).

EXAMPLE 1

This example illustrates one embodiment of a structure comprised of chambers and channels in which the method of the present invention can be practiced.

Figure 2:
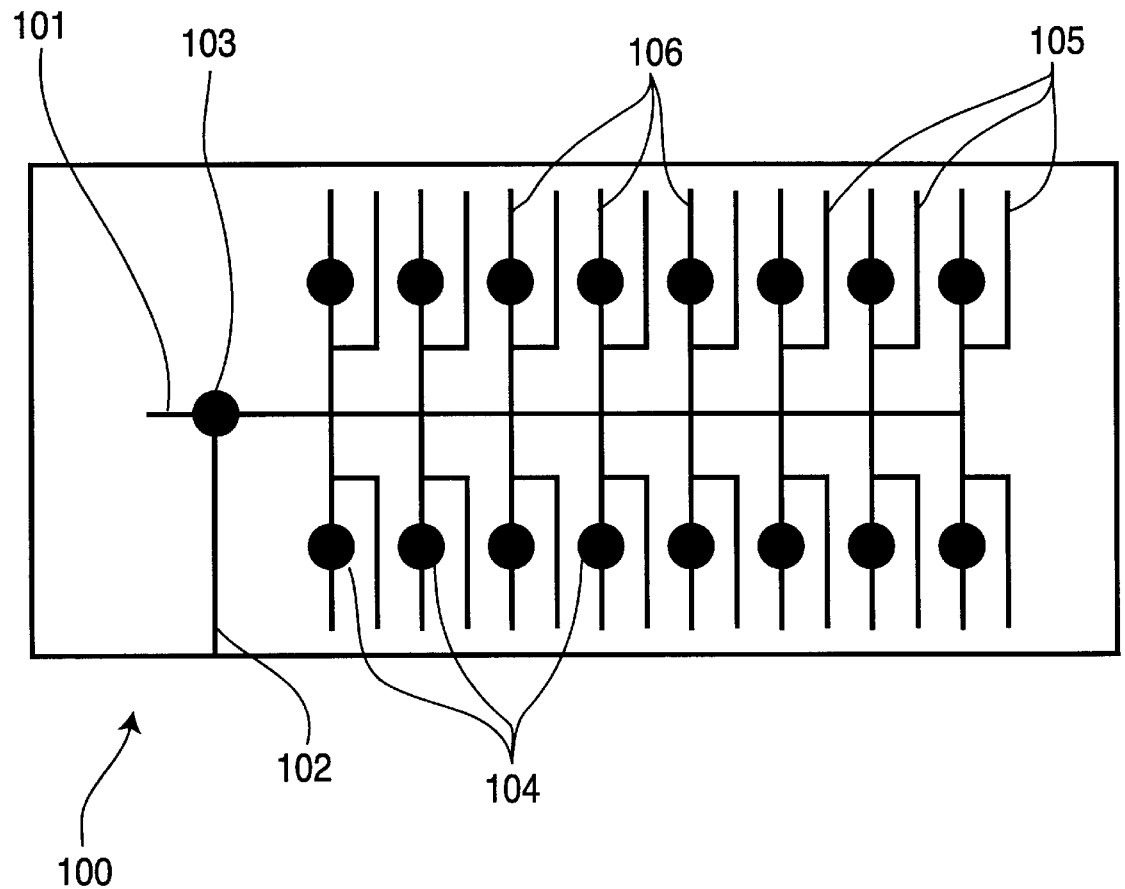
FIG. 2 depicts one embodiment of a device for multiple nucleic acid detection.

FIG. 2 depicts a structure 100 that is used to practice the present invention. Movement of fluids via pumps within the structure has been previously described in the aforementioned related applications. As shown, two channels 101 and 102 interface to the outside of the structure 100, respectively for input of (101) amplicon (i.e., first nucleic acid) that have avidin and a rhodamine tag attached thereto and (102) paramagnetic beads (substrate) that have biotin attached thereto, each of which are combined in an amplicon capture chamber 103 (a second chamber), wherein the amplicons attach to the beads by means of the avidin and biotin (binding moieties). A moveable magnet (not shown) on the outside of the structure 100 is used to sequentially move equal aliquots of the amplicon-bound beads into each first chamber 104; the parity of included amplicons in each chamber can be checked by measuring rhodamine-based fluorescent emission from each chamber. The aliquots of the amplicon-bound beads are kept in each first chamber 104 by means of a stationary magnet (not shown) located adjacent thereto for that purpose. Excess amounts (relative to the amount of amplicon present) of fluorescein-labeled probe is then pumped from one or more second chambers (not shown) via the channels 105 shown adjacent to each first chamber 104. The fluorescein-labeled probe is pumped into each first chamber 104, where conditions are provided that promote hybridization of complementary nucleic acids or binding of a nucleic acid-binding protein, depending on whether the probe used is a second nucleic acid or a protein. Following an appropriate period of incubation for the hybridization/binding, wash reagent is pumped through the same channels 105 through which the probe was previously pumped, provided from second chambers located elsewhere in the structure (not shown). All fluids displaced from the first chambers 104, including unhybridized/unbound probe, leave via waste channels 106 and are deposited into originally void second chambers (not shown). Finally, bound probe is measured by detection of fluorescein-based fluorescent emission from the first chambers 104.

EXAMPLE 2

The example illustrates the embodiment of the present invention directed to the identification of promoter mutations.

One purported class of promoter mutations involves the TATAA box. Whereas a wild-type promoter can have a sequence of 5'-TTGACA . . . TATAATG-3', a mutant promoter derived therefrom can have a sequence of 5'-TATACA . . . TAATATG-3'. The wild-type and mutant sequences are incorporated into separate oligonucleotides, which are then biotinylated using standard methods, that are used in the following manner:

Target DNA, such as nucleic acids selected by probing with a DNA binding protein, is denatured using heat or base. The biotinylated oligonucleotides are then added to the target DNA in separate reservoirs under conditions to promote annealing therebetween. Then superparamagnetic microparticles to which MutS protein is attached are combined with the annealed oligonucleotide-target DNA, such that the microparticles are caused to be captured in the reservoir by a magnet. Thereafter, the reservoir is washed to remove non-annealed and completely annealed oligonucleotides, and streptavidin-conjugated horseradish peroxidase is added to the reservoir. Finally, a color generating peroxidase assay is performed, wherein color generating in a reservoir indicates that a mismatched hybrid is contained therein. If the color generating reservoir had received the wild-type promoter sequence-including oligonucleotide, and the same target did not generate a color with the mutant promoter sequence-including oligonucleotide, then the assay identified a mutant promoter.

What is claimed:

1. A method for capturing a class of nucleic acids in a device, the method comprising:
    a. furnishing a device for relaying liquids in channels comprising the channels and one or more chambers;
    b. combining in a first chamber of the device (1) a population of nucleic acids comprised of nucleic acids of the class and (2) a probe that binds to the class of nucleic acids, the probe having an attachment moiety suitable for attaching to a first substrate on at least one paramagnetic or superparamagnetic microparticle, wherein the probe is a DNA binding protein or a repetitive nucleic acid element;
    c. forming one or more complexes of the probe and the class of nucleic acids;
    d. capturing the class of nucleic acids from the population of nucleic acids in the device by capturing the complex bound to the first substrate via an attachment of the moiety to the first substrate; and
    e. separating the class of nucleic acids bound to the first substrate from the unbound nucleic acids by (1) magnetically retaining the microparticles in one said chamber and moving through at least one of said channels liquid containing the unbound nucleic acids to another said chamber or (2) magnetically moving through at least one of said channels the microparticles from one said chamber to another.

2. The method of claim 1, wherein the nucleic acids of the population are RNA or DNA.

3. The method of claim 2, wherein the nucleic acids of the population are nuclease products or amplicons.

4. The method of claim 1, wherein the first chamber has a volume of from about 0.05 $\mu$l to about 250 $\mu$l.

5. The method of claim 1, wherein the microparticle is superparamagnetic.

6. The method of claim 1, wherein the probe binds preferentially to a specific sequence.

7. The method of claim 1, wherein the probe is a DNA binding protein which is Sp1, C-FOS, WT-1, or CRO.

8. The method of claim 1, wherein the nucleic acid, the probe, or first substrate includes an indicator moiety, provided that distinguishable indicator moieties are used when at least two of the nucleic acid, the probe and first substrate include an indicator moiety.

9. The method of claim 1, further comprising detecting the complex, wherein the detecting of the complex comprises exposing a detector to the complex, wherein the detector is a detector of radiation, fluorescence, or light.

10. The method of claim 1, wherein the probe is distributed to two or more first chambers, wherein the probe in one first chamber binds to a different class of nucleic acids than does the probe included in a different first chamber.

11. The method of claim 10, wherein the probe in each of the first chambers is placed in contact with the population of nucleic acids.

12. The method of claim 1, wherein the DNA binding protein preferentially binds to regulatory elements included in the population of nucleic acids.

13. The method of claim 1, further comprising:
   f. forming a second complex between (1) a second probe that binds to a second class of nucleic acids, the second probe having a second attachment moiety, and (2) the second class of nucleic acids; and
   g. capturing the second complex bound to a second substrate via the second attachment moiety.

14. The method of claim 13, wherein the second probe or the second substrate includes an indicator moiety, provided that distinguishable indicator moieties are used when both the second probe and the second substrate include an indicator moiety.

15. The method of claim 13, wherein aliquots of the second substrate-attached nucleic acids of the class are distributed to two or more first chambers.

16. The method of claim 15, wherein the aliquots in the respective first chambers are placed in contact with the probe, further wherein the probe in each of the chambers binds to different classes of nucleic acid.

17. The method of claim 1, further comprising.
   e'. magnetically moving the microparticle with the captured complex to a second chamber which is in fluid communication with the first chamber within the device to separate the class of nucleic acids from the remainder of the population of nucleic acids.

18. The method of claim 1, wherein the first substrate has an attached binding moiety, wherein the binding moiety and the attachment moiety preferentially or exclusively bind to each other to form a binding pair, thereby forming the attachment.

19. The method of claim 18, further comprising different substrates each having an appropriate binding moiety that attaches to a different probe, each probe having an appropriate corresponding attachment moiety.

* * * * *